United States Patent
Schuppert et al.

(10) Patent No.: US 8,355,874 B2
(45) Date of Patent: Jan. 15, 2013

(54) METHOD FOR IDENTIFYING PREDICTIVE BIOMARKERS FROM PATIENT DATA

(75) Inventors: Andreas Schuppert, Kürten (DE); Rolf Burghaus, Kaarst (DE); Christian Von Törne, Solingen (DE); Stephan Schwers, Köln (DE); Udo Stropp, Haan (DE); Harald Kallabis, Leverkusen (DE)

(73) Assignee: Bayer Technology Services GmbH, Leverkusen (DE)

( * ) Notice: Subject to any disclaimer, the term of this patent is extended or adjusted under 35 U.S.C. 154(b) by 1070 days.

(21) Appl. No.: 12/158,744

(22) PCT Filed: Dec. 11, 2006

(86) PCT No.: PCT/EP2006/011896
§ 371 (c)(1),
(2), (4) Date: Sep. 8, 2008

(87) PCT Pub. No.: WO2007/079875
PCT Pub. Date: Jul. 19, 2007

(65) Prior Publication Data
US 2009/0093689 A1     Apr. 9, 2009

(30) Foreign Application Priority Data
Dec. 22, 2005   (DE) .......................... 10 2005 062 163

(51) Int. Cl.
*G01N 33/48* (2006.01)
(52) U.S. Cl. ........................................................ 702/19
(58) Field of Classification Search .................... 702/19
See application file for complete search history.

(56) References Cited

OTHER PUBLICATIONS

Pittman et al., "Integrated Modeling of Clinical and Gene Expression Information for Personalized Prediction of Disease Outcomes," PNAS (2004) vol. 101, No. 22, pp. 8431-8436.*

* cited by examiner

*Primary Examiner* — Jerry Lin
(74) *Attorney, Agent, or Firm* — Norris McLaughlin & Marcus, P.A.

(57) ABSTRACT

The invention relates to a method for developing a biomarker for the prognosis of the result of a therapeutical treatment based on data obtained in clinical studies, data remaining unchanged by therapy being subdivided into diagnostic and genomic parameters and the marker being defined by a combination of parameters. The method according to the invention is characterized by specifying the maximum number of parameters for defining the marker and thus the maximum complexity of the system from the beginning and by carrying out the search for defining parameters by sequential combination of clinical parameters (=z parameters) and/or genomic parameters (=x parameters).

7 Claims, 2 Drawing Sheets

METHOD FOR IDENTIFYING PREDICTIVE BIOMARKERS FROM PATIENT DATA

Figure 1:
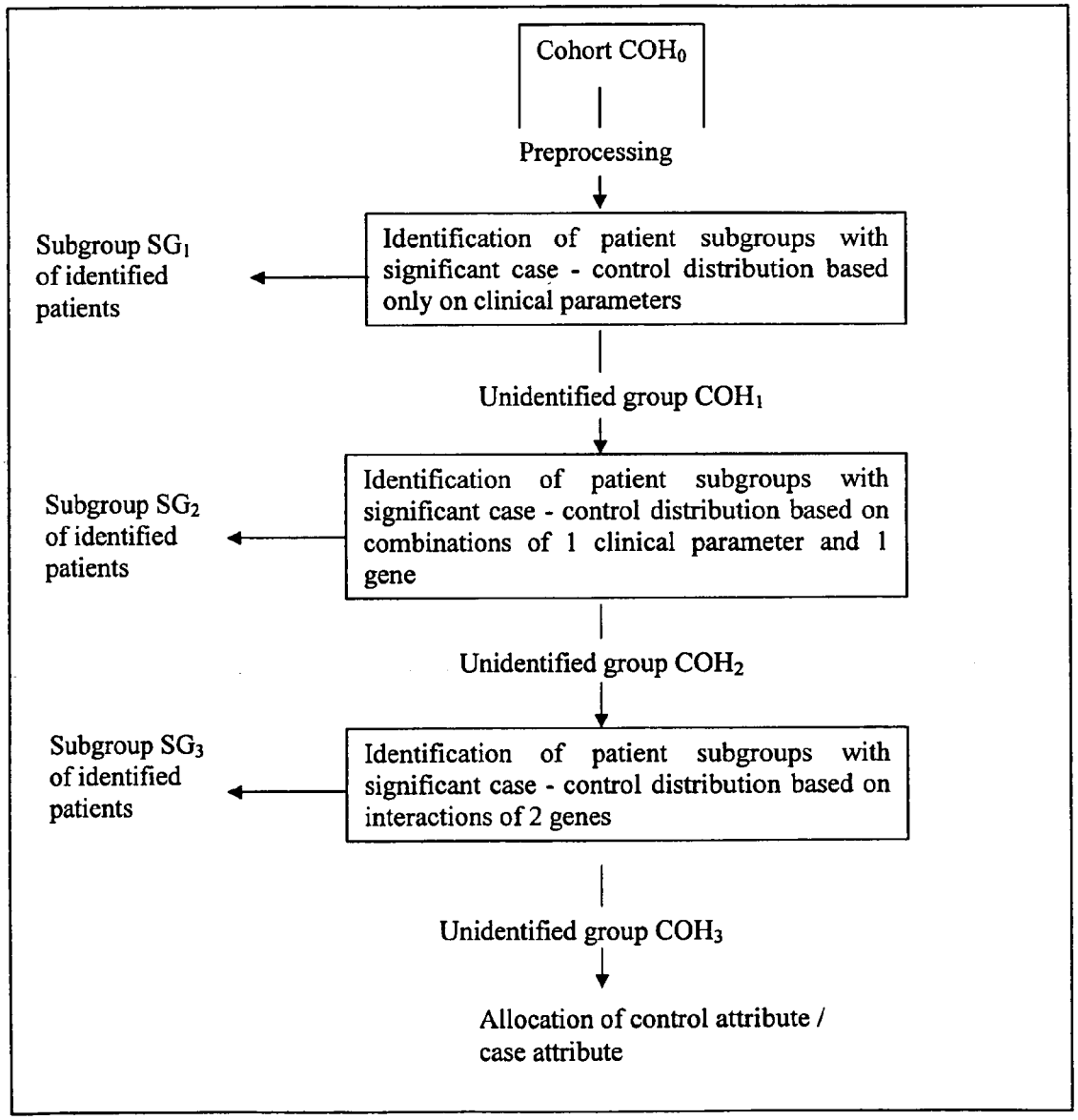

This application is a 371 of PCT/EP2006/011896, filed Dec. 11, 2006, which claims foreign priority benefit under 35 U.S.C. §119 of the German Patent Application No. 10 2005 062 163.5 filed Dec. 22, 2005.

The present invention relates to a method for developing a biomarker for prognosis of the result of a therapeutic treatment with the aid of data from clinical studies.

The identification of predictive biomarkers is an essential precondition for the further development of medicament therapies with a view to personalized medicine. The term biomarker refers not only to biological parameters measured directly from clinical diagnosis, gene diagnostics, etc., but also computation methods which allow a diagnosis to be made from suitable combinations of a sizeable number of measured values of different biological parameters, or make it possible to calculate a prognosis for the clinical response to a therapy. The finding of such complex biomarkers in practice is often extremely unreliable or even impossible owing to the great variety of possible biological parameters, which often exceeds significantly the number of subjects in clinical studies. This problem is well known in pattern recognition by the key term "curse of dimensionality" and can be resolved only to a very limited extent by increasing the subject cohorts.

Established methods for overcoming this problem are cross-validation and bootstrapping (M. Berthold, D. J. Hand, Intelligent Data Analysis, Springer, Heidelberg 1999, pp. 56-57). These methods effectively prevent excessive restriction of parameters, but they allow only little complexity in the combinations of parameters which could be tested in order to identify a potential biomarker, and therefore they do not allow the full potential of a genomic, transcriptomic or proteomic data set to be evaluated for the diagnosis of complex diseases or prognosis of reactions to therapeutic treatments.

One established method for assessing the significance of a biomarker is to analyze the underlying mechanism and the structure of the system. If the structure parameters of the system are known, the prognosis reliability of the model can be improved significantly (A. Schuppert, Extrapolability of structured hybrid models: A key to optimization of complex processes. In B. Fiedler et al., editor, International Conference on Differential Equations, pages 1135-1151. World Scientific Publ., Singapore, 2000; B. Fiedler, A. Schuppert, Local Identification of scalar hybrid models with tree structure, preprint, FU Berlin, 2004). WO 03/042702 A1 describes a method which does not depend on quantification of the interaction but nevertheless still requires a large data set and the interactions between parameters in the form of a tree. Other methods in turn do not require representation of the interactions in the form of a tree, but do require quantification of the interactions (J. J. Rice, G. Stolovitzky, Making the most of it: pathway reconstruction and integrative simulation using the data at hand, DDT: BIOSILICO, Vol. 2, No. 2, March 2004, 70-77).

These methods are used to analyze interaction networks between equal hierarchical levels, i.e. gene-gene interaction networks or protein-protein interaction networks, although they are not suitable for the identification of interaction networks between genomic parameters and clinical data. Owing to this, there is still a lack of structural data concerning genome-based biomarkers for clinical applications.

J. Pittmann et al. (J. Pittmann et al., Integrated modeling of clinical and gene expression information for personalized prediction of disease outcomes, PNAS Jun. 1, 2004, Vol. 101, no. 22, 8431-8436) have recently achieved a significant improvement in determination of the repetition risk for breast cancer by the combination of gene expression markers and clinical diagnostic parameters. It has been possible to improve the informativeness of a biomarker for prognosis of the clinical effect significantly by integrating genomic and clinical data in a complex biomarker. The data structure became more complex in this approach, however, and the risks of "overfitting" or reliability losses in the analysis were increased. In the case described, these risks were compensated for significantly by improving the quality of the marker, although this need not always be the case.

A systematic method for developing such biomarkers from the data of clinical studies, which allows a significantly lower complexity than the current methods, would therefore be desirable in order to provide the doctor with more accurate diagnostic aids for the individual patient responses to a medicament therapy.

The object is achieved by a systematic hierarchical subgroup search with hierarchization of the parameter types. In the present invention, complex biomarkers are provided by the sequential combination of clinical and genomic data. The sequential combination keeps the increase in the complexity of the data structure within limits, and surprisingly minimizes the "overfitting" risk.

The present invention therefore provides a method for developing a biomarker for prognosis of the result of a therapeutic treatment with the aid of data from clinical studies, the data unmodified by the therapy being divided into diagnostic and genomic parameters and the marker being defined by a combination of parameters, characterized in that a. The maximum number of parameters for definition of the marker, and therefore the maximum complexity of the system, is established from the start, b. The search for defining parameters is carried out by sequential combination of clinical parameters (=z parameters) and/or genomic parameters (=x parameters).

In a first step, based merely on the clinical—diagnostic parameters, subgroups are searched for which statistically significantly allow clearcut formation of subgroups of subjects with a unique phenotype. This subject group is separated from the total cohort.

For the other subjects, clinical parameters are searched for which likewise respectively allow a unique prognosis by combination with the genotyping on a single gene.

For those subjects who cannot be analyzed in the first two steps, a hybrid model is compiled which permits sufficient prognosis by combining the genotyping of a plurality of genes.

For prognosis purposes in this case, it is only possible to use those parameters which have been recorded in the screening phase before the start of the therapy or which cannot be influenced by the therapy:

The clinical/diagnostic parameters are referred to as "z" parameters and the genomic parameters form the "x" parameters.

The method according to the invention starts at the clinical data level. Subject groups with unique clinical reactions are identified in the analysis with the aid of their clinical z parameters and subgroups are formed. The method according to the invention increases step-by-step the ratio number of x parameters/number of z parameters in the parameter set; the complexity c of the parameter set, i.e. the number of parameters which are identified in order to define the marker, remains the same throughout the method.

A subgroup is deemed predictive if $q > Q_0$ is satisfied when a predefined quality q of the clinical reaction is compared with the predefined requirements $Q_0$. The quality q is, for example the value p of the z parameter for the subgroup compared with the value of all subjects, calculated with the aid of a test set.

The method according to the invention starts with the clinical data (=z parameters) and operates sequentially with the following steps:

a. Input of the subject group $COH_0$, its z parameters and x parameters, and input of the quality requirement $Q_0$ for the clinical applicability requirements. Also input of the allowed total complexity c (=maximum number of parameters which may be combined with one another in the method, and are subsequently used for definition of the marker). The total complexity c is usually at most 10, and will be adapted to the size of the data set. Values of up to 4 are preferably selected for the total complexity c, since according to experience the risk of a false positive result increases significantly beyond this. A total complexity c>4 is preferred when either there are very large data sets or extremely elaborate validation methods are used.
b. Search for one or more sets of from 1 to c clinical parameters which characterize a subgroup of subjects $SG_1$, a quality q of whose clinical reaction has the quality requirements q>$Q_0$. The total complexity is increased iteratively during the identification process so long as the method finds a subgroup, and up to a maximum allowed total complexity c. The clinical reaction of all subjects in the subgroups $SG_1$ can then be prognosed with the aid of the z parameters alone.
c. These subjects are excluded from the subject group $COH_0$, so that a new subject group $COH_1$ is defined as $COH_0$ minus $SG_1$.
d. Search for one or more sets of (c-1) z parameters and one x parameter which characterize a subgroup of subjects $SG_2$, a quality q of whose clinical reaction has the quality requirements q>$Q_0$. The clinical reaction of all subjects in the subgroup SG2 can be prognosed with the aid of the clinical parameters and a genomic parameter.
e. These subjects are excluded from the subject group $COH_1$, so that a new subject group $COH_2$ is defined as $COH_1$ minus $SG_2$.
f. Search for one or more sets of (c-n) z parameters and n x parameters, where n=0 to c, which characterize a subgroup of subjects $SG_{+1}$, a quality q of whose clinical reaction has the quality requirements q>$Q_0$.
g. Definition of the subject group $COH_{n+1}$ as $COH_n$ minus $SG_{n+1}$.
h. Repetition of steps f) to g) until no subgroups are found or n=c,
i. The subjects who cannot in the end be assigned to any subgroup SGx with a quality q, where q>$Q_0$, form a remainder group $COH_R$.
j. Output of a list of the identified markers and a list of subjects who belong to the remainder group $COH_R$.

Identification of the subgroups SGx may be achieved by various methods, for example decision trees, X (support vector machines) or association rules (M. Berthold, D. J. Hand, Intelligent Data Analysis, Springer, Heidelberg 1999, pp. 195-215). These established methods alone, however, are not capable of preventing the combinatorial explosion in the number of possible subgroups SGx, if the complexity c i.e. the number of parameters for defining the marker is allowed to increase.

In a particular embodiment of the method, the subgroup SGx is subdivided (FIG. 1):
1.) Subjects who show the desired clinical response form a control group (controls), and
2.) Subjects who show side effects form a cases group (cases).

Figure 2:
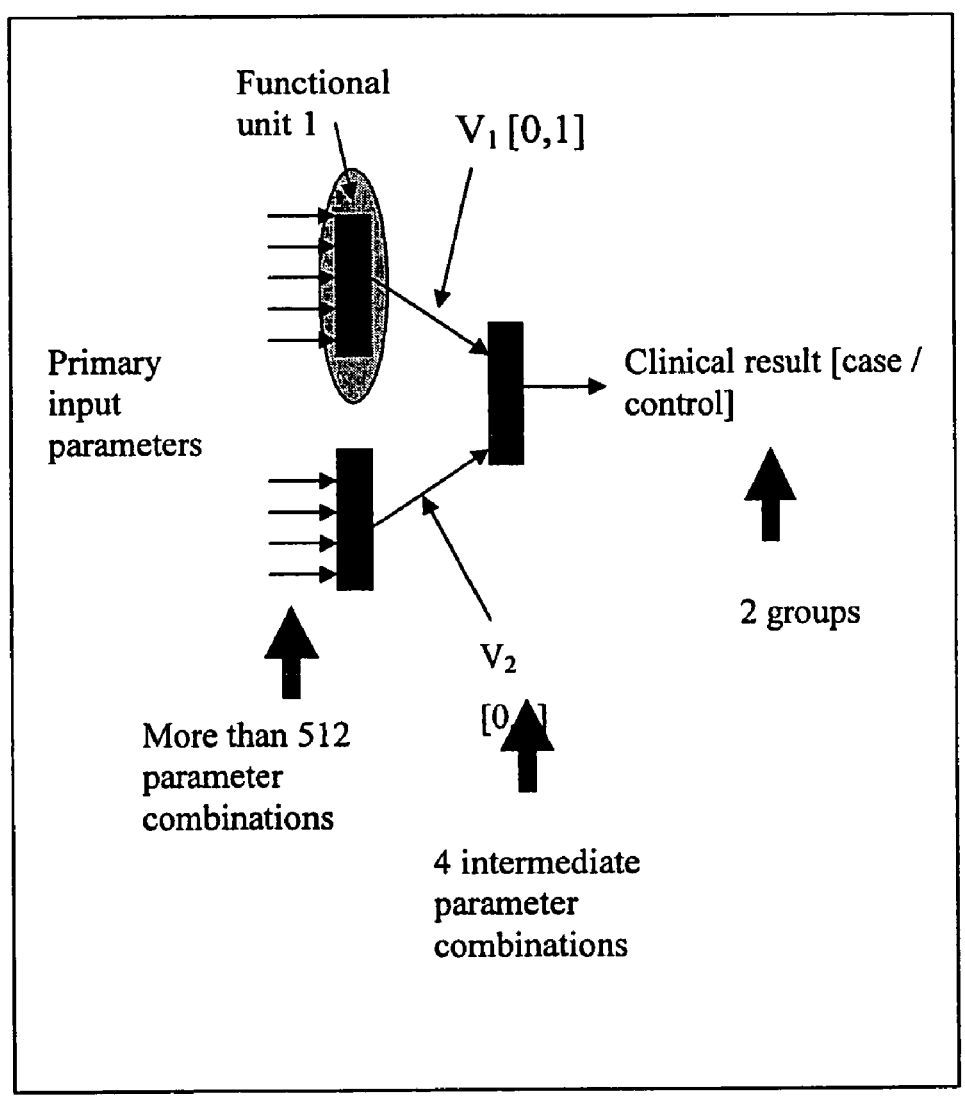

If the x parameters are discrete or discretized, in a particular embodiment of the method the combinatorial explosion in the number of possible subgroups SGx can be reduced by compressing the x parameters with the following method:

If there are $x_1 \ldots x_n$ parameters with discrete values $m_1 \ldots m_n$, then $*m_1 \ldots *m_n$ subgroups SGx are possible which must be studied for a unique distribution of z parameters. In many cases, the contribution of a single parameter or a parameter group to the clinical reaction can be restricted to a limited number of active values v of intermediate parameters—referred to below as "metastates". These metastates are not directly observed, but in the ideal case can be described by binary values 0 and 1 (FIG. 2). If such a restriction is acceptable, not all subgroups SGx are actually relevant for the clinical reaction. All combinations of values m, which lead to the same active value v, can be combined to form a "metastate" which is described only by the value v.

The method can then concentrate on these "metastates" and their combinations. If the number of metastates<<the number of parameters x, the complexity c of the marker can be reduced significantly and the method is then carried out with the following steps:
1) identification of all parameter value combinations which leads t the same active value v for the definition of "metastates",
2) the subgroup analysis is carried out according to Steps 1 to 4 with the aid of the metastate values v.

Step 1 (=identification of metastates) is carried out with standard combinatorial optimization routines, for example genetic algorithms, X (simulated annealing), Monte Carlo search or Y (steepest descent). In each step of the combinatorial optimization routine, a subgroup analysis takes place with evaluation of the quality q of the clinical reaction. The aim of the optimization routine is to identify the correlation between values of the x parameter and v values of the metastate, which lead to an optimization of the quality q in Step 2.

Although this hierarchical structuring of the subgroup analysis with the aid of projection onto metastates requires greater numerical processing, it can nevertheless lead to a dramatic reduction in the number of possible subgroups by combining the individual parameter values, which leads to a significant improvement in the reliability and prognosis quality of the marker.

In another embodiment of the method, a validation step is carried out in which, with the aid of the Monte Carlo method, a test is performed by randomization as to whether the automatic search in a randomized set of subjects leads to the same subgroups. The subgroup SGx is assigned a prognosis reliability (=significance) pr which represents the clinical applicability of the marker.

A prognosis reliability pr may also be assigned for all subjects in the subject group $COH_R$, so that the clinical applicability of the marker for the remainder group can be assessed. If for example a false positive prognosis leads to an intolerable risk for the subject, then "not classifiable" may be output as a result for the remainder group if there is insufficient prognosis reliability.

Any desired quality measure for the prognosis may in this case be selected as the prognosis reliability pr, for example sensitivity and specificity in the test group. These values may be found with the aid of cross-validation on a test data set selected according to the random principle.

As an alternative measure, it is possible to use the probability that the quality measure such as sensitivity and specificity can be interpreted as a random result (p value). The latter may, for example, be determined with the aid of bootstrapping methods.

It has been shown that the hypothesis, that the identified subgroups have been formed falsely and purely by chance, can be excluded with a prognosis reliability/significance p<0.02. The prognosis reliability/significance p is the estimated probability that the classification can be attributed to a random event. It may be estimated with the aid of a bootstrap method. Results of a data analysis for which p<0.05 applies are in this case denoted as significant; p values <0.01 are particularly preferred.

With the method according to the invention, it is possible to identify markers for clinical reactions which are defined by diagnostic and/or genomic parameters, and whose sensitivity and prognosis reliability is more than 80% sensitivity and 98% specificity, preferably from 80% to 85% sensitivity and 97.9-98.5% specificity. These values are prognosis values, which have been found with the aid of cross-validation on a test data set selected according to the random principle. With the aid of bootstrapping methods, p values <2% can be measured for the probability that the results found are based on a random event.

Advantages of the method are the structured classification in a plurality of steps, in each step a systematic change being made from a classification based on purely clinical data to a classification on purely genome-based data with strict control of the complexity of the classifiers used on a low level. In this way, on the one hand, it is possible to achieve a significantly improved performance of the classification measured in specificity and sensitivity, and on the other hand a significant improvement in the statistical significance measured in p values for the classification results with the aid of bootstrap methods or cross-validation.

FIGURES

FIG. 1: Example of the sequential identification workflow with complexity c=2

FIG. 2: Example of reduction in the complexity, starting from the primary parameters (x) in favor of the clinical result (z) with the aid of an intermediate projection in step with two functional intermediate units.

EXAMPLE

The method was tested with the aid of an association study into the toleration of statins, without being restricted thereto.

The method according to the invention enabled the prognosis of ADR phenotypes from a combination of priori measured clinical parameters and genotyping, using in total the measurement of 4 clinical parameters and 25 SNPs distributed over 12 genes. It was possible to find other combined markers, which show weaker but still reliable performance with virtually the same measurement outlay.

Statins are the most frequently prescribed drugs, and are used to reduce the cholesterol level. The drug side effects (ADR, Adverse Drug Reactions) associated with statins mostly relate to the skeletal musculature; muscle pain may occur in 0.6-3% of patients and in rare cases so-called rhabdomyolysis, leading to acute kidney failure. Owing to 1) the widespread use of statins and 2) the gravity of the possible side effects, it would be desirable to have a diagnostic test which can identify patients who have statin intolerance before the start of therapy. Statin-induced ADRs could thus efficiently be avoided. Furthermore, the doctor would be able to select a more compatible form of therapy early on.

A subject study, in which 312 subjects were genotyped, was analyzed by the method.

The following clinical parameters (of the multiplicity of subjects) were furthermore recorded:
'SEX' 'BORN' 'HEIGHT' 'WEIGHT' 'BMI' 'SBP' 'DBP' 'CONC' 'CONSENT' 'CK_SCR' 'CK_SCRLATER' 'CK_TTLATER' 'CK_TT_V2ORV3' 'LDL_SCR' 'HDL_SCR' 'TRIGLY_SCR' 'CHOL_SCR' 'SGOT_SCR' 'SGPT_SCR' 'ALKPHOS_SCR' 'LDL_LATER' 'HDL_LATER' 'TRIGLY_LATER' 'CHOL_LATER' 'SGOT_LATER' 'SGPT_LATER' 'ALKPHOS_LATER' 'LDL_RESP'

For prognosis purposes in this case, it is only possible to use those parameters which have been recorded in the screening phase before the start of the therapy or which cannot be influenced by the statin therapy:
'SEX' 'HEIGHT' 'WEIGHT' 'BMI' 'CK_SCR' 'LDL_SCR' 'HDL_SCR' 'TRIGLY_SCR' 'CHOL_SCR' 'SGOT_SCR' 'SGPT_SCR' 'ALKPHOS_SCR'

Two subject cohorts were formed:
1.) Patients with good statin tolerance (controls), and
2.) Patients for whom side effects were observable after statin administration (cases).

In order to increase the contrast between the cases group and control group, the analysis included only case patients who are characterized as more than 83 by their 'CK_TT_V2ORV3' value so that an ensemble of 144 cases and 144 controls was available in total. The result per se was not affected by this.

The patients were characterized during after the therapy according to the occurrence of rhabdomyolysis, in particular an elevated CK value. To this end, the parameter 'CK_TT_V2ORV3'
was employed and phenotyped by DS.

SNP Data Compression—Definition of Metastates

As SNP genotyping data, 3632 SNPs on 86 genes were available, the distribution of the SNPs on the genes varying greatly. Among the SNP data provided, only those SNPs which could be measured with sufficient frequency were taken into account. Of these, the SNP expressions "AC", . . . were coded numerically by giving the number 1 to the expression of the $1^{st}$ patient in the file, giving the number 2 to the next occurring expression, etc. The analysis methods were configured so that the pseudo-correlation thereby occurring (SNP expression 3 frequent in controls) was not relevant.

SNP data concerning 8 new genes were subsequently provided, these being processed similarly so that a total of 94 candidate genes, which could play a role in the occurrence of statin-induced ADRs owing to their function in human metabolism, were selected for carrying out the study.

The original SNP expressions were now compressed on each gene by assigning a number to every combination of SNP expression on each individual gene. Since a prediction would have been made extremely difficult by the large number of possible combinatorial SNP expressions, a direct number was allocated only to those SNP combinations on each gene which occurred at least 6 times. At most 15 SNP combinations therefore occurred on each gene.

All rarer SNP combinations, i.e. all combinations which occurred fewer than 5 times in the subject cohort, were replaced by an SNP combination which occurred at least 5 times and exhibited the least Euclidean distance from the corresponding rare SNP combination, i.e. it received the number of the SNP combination that had the greatest similarity in each case (Hamming distance). The result is an individual mapping of each SNP combination with a discrete value s, which increases the statistical relevance of the combination. Since information is at most eliminated by this compression, it cannot lead to any bias.

As a result, a table is obtained in which a number $s_j(g_k)$=[1..., number of SNP combinations on gene k] on each gene gk is entered for each subject j, which corresponds to the SNP expression of the subject on the respective gene and which (apart from the compression) can be inverted to give the SNPs.

Further Selection of the Subject Group

In a first step, based merely on the clinical—diagnostic parameters, subgroups are searched for which statistically significantly allow clearcut formation of subgroups of subjects with a unique phenotype.

Since the ck level has a critical effect on the ADR expression, all patients for whom there was no information about the ck level before therapy (ck-scr) were removed from the subject cohort in a preprocessing step. A cohort of 179 patients (91 cases, 88 control) remained for the further processing.

The Combigene Method

1) Classification of the Patients Based Only on Clinical Data

In Method Step 1, subgroups were searched for which uniquely have a clinical reaction with high statistical significance $p<0.01$ and complexity$\leq 3$. The search methods of decision trees, X (support vector machines) or association rules (M. Berthold, D. J. Hand, Intelligent Data Analysis, Springer, Heidelberg 1999, pp. 195-215) were used for this step.

A single informative subgroup was identified, which is described in the following way:

Rule 1: All patients with ck level>80 before therapeutic treatment showed side effects after statin administration. This rule applies for 35 out of 179 subjects and is highly informative.

The prognosis reliability/significance of the rule was estimated at $p<0.001$ by the Monte Carlo method.

These subjects were excluded from the cohort, the new cohort $COH_1$ consisting of 56 cases and 88 controls.

2) Classification of the Patients Using the Combination of 1 Clinical Parameter and 1 Gene In Method Step 2, subgroups were searched for which uniquely have a clinical reaction with a parameter combination of one clinical parameter and one gene (complexity=2). Since clinical parameters have continuous values and genomic parameters have discrete values, the possible subgroups in each combination were described in the following way:

Characterization of the cases and controls was therefore carried out with the aid of a combination of the clinical parameters and the genotyping. The aim was to characterize subject groups with the aid of the clinical parameters in such a way that a subgroup of the cases or a subgroup of the controls in each subject group is characterized without error with the aid of the SNP data on a single gene.

The set of clinical parameters was artificially divided into high and low values. For each range, a test was carried out as to whether there was a genomic value s to describe the corresponding gene, which comprises the subgroup of subjects with a valid reliability ($p<0.0001$), i.e. how many of the 144 subjects of the cohort $COH_1$-56 cases or 88 controls—have the particular clinical parameter and the genomic value.

In a validation step, a test was carried out by randomization with the aid of the Monte Carlo method, as to whether the automatic search in a randomized set of subjects leads to the same subgroups. It has been shown that the hypothesis, that the identified subgroups have been formed falsely and purely by chance, can be excluded with a prognosis reliability/significance $p<0.02$. In this case "p" is the probability estimated with the aid of a bootstrap method that the classification can be attributed to a random event.

As a result of the subgroup method, 4 groups of parameters were found with this high statistical significance, each of which consists of one clinical parameter and the SNP expression (uniquely characterized by the confirmation of respectively 1 or more SNPs) in each case on 1 gene, and which allow case/control typing in each group. These groups may be characterized by low LDL_SCR HDL_SCR, CHOL_SCR and high ALK_Phos values on the clinical side and 9 SNPs on 4 genes in all.

The overall typing on these groups therefore requires the measurement of at least 9 SNPs in total to carry a unique characterization of the relevant SNP expressions on the respective genes. 44 cases and 41 controls could be classified by this method, which form the cohort $COH_2$.

3) Classification of the Subjects Using a Combination of Sets of 2 Interacting Genes In this new cohort, a search was made in the last step of the analysis for a subgroup characterized by a combination of up to 2 genes (complexity=2). Moreover, no purely genotype-based subgroup with a complexity 1 (a single gene for characterizing the marker) was found.

For the subject group $COH_2$, it was assumed that there are no single dominant genes among the measured genes, rather the expression of the phenotypes is due to a combination of "poor" SNP states on different genes.

With the aid of 2-fold combinations of gene expressions ("gene doublets"), it was possible to characterize a sufficient number of statistically highly significant gene groups which, in combination with the preselection, allow sufficient prediction of cases. The worst-case principle was always adopted as a procedure: a subject is prognosed as a "case" with the aid of a gene doublet only if they have a "poor" SNP state in the expression of both genes. The maximum number of cases which could be characterized per gene doublet with high significance lay between 18 and 25% of the total number of cases.

A search was made for the smallest possible groups of "gene doublets" which, in combination, characterized a maximally large number of cases reliably and stably (i.e. with 90% probability in the test set); the false positive rate was meant to remain <2% in total. The gene groups were furthermore selected so that the characterization could be carried out with a minimal number of genotypings. Only gene doublets which could characterize more than 18% of the cases in the test set were therefore taken into consideration. The cases are selected according to the following algorithm:

calculate the prognosable case group for each gene doublet of the group if a subject with a gene doublet of the group is identified as a case, then they are characterized as a case.

It was possible to find a total of 32 (40 with the 8 additional genes) groups of 4 gene doublets (Table 2) which permit sufficient characterization (Table 1):

Absolute values are respectively indicated, i.e. 0.83 corresponds to 83%.

Gene group Number 31, with the following 4 gene doublets, is particularly interesting:

15/21 number of SNPs required: 2/1
29/84 number of SNPs required: 2/2
34/76 number of SNPs required: 2/2
49/59 number of SNPs required: 2/3

Their performance, measured in sensitivity and selectivity by cross-validation, is optimal among the groups found so far.

It turns out that a large number of gene groups have a very similar performance, which actually differs only in a few gene doublets.

It is conspicuous that gene 74 occurs very frequently and even forms a "doublet" with itself. The implication is that this gene on its own allows typing of a further subgroup. Addition of the 8 extra genes provided no new results; significantly new results could be found neither in the preselection nor in the combigene method. The only new combinations contained gene doublets with genes 74/88 or 74/90, and there was only 1 significant variable SNP state to be found in genes 88 and 90. These doublets are therefore equivalent to the 74/74 doublet and offer no new information.

In no case could runs with phenotype data distributed in a randomized fashion replicate the performance which was achieved with the original data.

Adding further genes to the gene doublets, to form gene triplets or quadruplets, could not achieve any statistically significant improvement in the performance, although it cannot be ruled out that the significance is greatly underestimated owing to the limitingly small number of subjects.

TABLE 1

| Group No. | Sens. | (1-Selectivity) |
|---|---|---|
| 1.0000 | 0.8242 | 0.0135 |
| 2.0000 | 0.8242 | 0.0135 |
| 3.0000 | 0.8242 | 0.0135 |
| 4.0000 | 0.8242 | 0.0135 |
| 5.0000 | 0.8242 | 0.0137 |
| 6.0000 | 0.8242 | 0.0141 |
| 7.0000 | 0.8242 | 0.0141 |
| 8.0000 | 0.8242 | 0.0141 |
| 9.0000 | 0.8242 | 0.0141 |
| 10.0000 | 0.8242 | 0.0197 |
| 11.0000 | 0.8242 | 0.0197 |
| 12.0000 | 0.8242 | 0.0197 |
| 13.0000 | 0.8242 | 0.0197 |
| 14.0000 | 0.8462 | 0.0146 |
| 15.0000 | 0.8352 | 0.0173 |
| 16.0000 | 0.8352 | 0.0173 |
| 17.0000 | 0.8352 | 0.0173 |
| 18.0000 | 0.8352 | 0.0173 |
| 19.0000 | 0.8242 | 0.0143 |
| 20.0000 | 0.8242 | 0.0200 |
| 21.0000 | 0.8352 | 0.0175 |
| 22.0000 | 0.8242 | 0.0135 |
| 23.0000 | 0.8242 | 0.0141 |
| 24.0000 | 0.8242 | 0.0197 |
| 25.0000 | 0.8352 | 0.0173 |
| 26.0000 | 0.8352 | 0.0177 |
| 27.0000 | 0.8352 | 0.0140 |
| 28.0000 | 0.8242 | 0.0163 |
| 29.0000 | 0.8242 | 0.0131 |
| 30.0000 | 0.8462 | 0.0120 |
| 31.0000 | 0.8571 | 0.0192 |
| 32.0000 | 0.8352 | 0.0165 |

TABLE 2

| Group No. | GD 1 | | GD 2 | | GD 3 | | GD 4 | |
|---|---|---|---|---|---|---|---|---|
| 1 | 34 | 76 | 46 | 51 | 74 | 74 | 11 | 21 |
| 2 | 34 | 76 | 46 | 51 | 60 | 74 | 11 | 21 |
| 3 | 34 | 76 | 46 | 51 | 57 | 74 | 11 | 21 |
| 4 | 34 | 76 | 46 | 51 | 56 | 74 | 11 | 21 |
| 5 | 31 | 74 | 34 | 76 | 46 | 51 | 11 | 21 |
| 6 | 29 | 84 | 46 | 51 | 74 | 74 | 11 | 21 |
| 7 | 29 | 84 | 46 | 51 | 60 | 74 | 11 | 21 |
| 8 | 29 | 84 | 46 | 51 | 57 | 74 | 11 | 21 |
| 9 | 29 | 84 | 46 | 51 | 56 | 74 | 11 | 21 |
| 10 | 29 | 84 | 34 | 76 | 49 | 59 | 74 | 74 |
| 11 | 29 | 84 | 34 | 76 | 49 | 59 | 60 | 74 |
| 12 | 29 | 84 | 34 | 76 | 49 | 59 | 57 | 74 |
| 13 | 29 | 84 | 34 | 76 | 49 | 59 | 56 | 74 |
| 14 | 29 | 84 | 34 | 76 | 46 | 51 | 11 | 21 |
| 15 | 29 | 84 | 34 | 76 | 46 | 51 | 74 | 74 |
| 16 | 29 | 84 | 34 | 76 | 46 | 51 | 60 | 74 |
| 17 | 29 | 84 | 34 | 76 | 46 | 51 | 57 | 74 |
| 18 | 29 | 84 | 34 | 76 | 46 | 51 | 56 | 74 |
| 19 | 29 | 84 | 31 | 74 | 46 | 51 | 11 | 21 |
| 20 | 29 | 84 | 31 | 74 | 34 | 76 | 49 | 59 |
| 21 | 29 | 84 | 31 | 74 | 34 | 76 | 46 | 51 |
| 22 | 25 | 74 | 34 | 76 | 46 | 51 | 11 | 21 |
| 23 | 25 | 74 | 29 | 84 | 46 | 51 | 11 | 21 |
| 24 | 25 | 74 | 29 | 84 | 34 | 76 | 49 | 59 |
| 25 | 25 | 74 | 29 | 84 | 34 | 76 | 46 | 51 |
| 26 | 15 | 21 | 34 | 76 | 49 | 59 | 11 | 21 |
| 27 | 15 | 21 | 34 | 76 | 46 | 51 | 11 | 21 |
| 28 | 15 | 21 | 29 | 84 | 49 | 59 | 11 | 21 |
| 29 | 15 | 21 | 29 | 84 | 46 | 51 | 11 | 21 |
| 30 | 15 | 21 | 29 | 84 | 34 | 76 | 11 | 21 |
| 31 | 15 | 21 | 29 | 84 | 34 | 76 | 49 | 59 |
| 32 | 15 | 21 | 29 | 84 | 34 | 76 | 46 | 51 |

Result

The method according to the invention therefore enabled the prognosis of ADR phenotypes from a combination of priori measured clinical parameters and genotyping, using in total the measurement of 4 clinical parameters and 25 SNPs distributed over 12 genes. It was possible to find other combined markers, which show weaker but still reliable performance with virtually the same measurement outlay.

The markers produced by the method according to the invention show a performance of 80% sensitivity and 98% specificity. These performance data were tested in the last step with the aid of cross-validation; furthermore, with the aid of bootstrapping in Steps 1 and 2, p values<1% ($1^{st}$ step) and p<2% in the second step were determined.

The invention claimed is:

1. A method for developing a biomarker for prognosis of the result of a therapeutic treatment with the aid of data from clinical studies, the data unmodified by the therapeutic treatment being divided into clinical and genomic parameters and the marker being defined by a combination of parameters, said method comprising the following steps:
   a. Inputting to a computer:
      i. a subject group $COH_0$, its z parameters and x parameters,
      ii. a quality requirement $Q_0$ for the clinical applicability requirements,
      iii. an allowed total complexity c,
   b. Searching for a set of from 1 to c clinical parameters which characterizes a subgroup of subjects $SG_1$, a quality q of whose clinical reaction has quality requirements $q>Q_0$,
   c. Defining a subject group $COH_1$ as $COH_0$ minus $SG_1$,
   d. Searching for one or more sets of (c-1) z parameters and one x parameter which characterize a subgroup of subjects $SG_2$, a quality q of whose clinical reaction has the quality requirements $q>Q_0$,
   e. Defining a subject group $COH_2$ as $COH_1$ minus $SG_2$,
   f. Searching for one or more sets of (c-n) z parameters and n x parameters, where n=0 to c, which characterize a subgroup of subjects $SG_{n+1}$, a quality q of whose clinical reaction has the quality requirements $q>Q_0$,
   g. Defining a subject group $COH_{n+1}$ as $COH_n$ minus $SG_{n+1}$, h. Repeating steps f) to g) until no subgroups are found or n=c, i. Forming a remainder group $COH_R$, and j. Outputting from the computer a list of identified markers and a list of subjects of the remainder group $COH_R$.

2. The method for developing a biomarker as claimed in claim 1, wherein a subgroup SGx is subdivided into a control group (controls) and a cases group (cases).

3. The method for developing a biomarker as claimed in claim 1, wherein the parameter values are discrete or discretized, and the number of x parameters is reduced to a limited number of active values v (=metastates).

4. The method for developing a biomarker as claimed in claim 1, wherein a prognosis reliability is assigned to a subgroup SGx.

5. The method for developing a biomarker as claimed in claim 4, wherein sensitivity and specificity in the test group are selected as the prognosis reliability.

6. The method for developing a biomarker as claimed in claim 5, wherein the prognosis reliability of the marker is more than 80% sensitivity and 98% specificity.

7. The method for developing a biomarker as claimed in claim 6, wherein the prognosis reliability of the marker is from 80 to 85% sensitivity and 97.9 to 98.5% specificity.

* * * * *